United States Patent
Booker et al.

(10) Patent No.: US 8,163,252 B2
(45) Date of Patent: Apr. 24, 2012

(54) KIT FOR TAKING BIOPSIES, AUTOPSIES, EXCISIONS, AND RESECTIONS AND METHODS THEREOF

(75) Inventors: David L. Booker, Augusta, GA (US); Stephen Mark Repko, Augusta, GA (US); Kimberly A. Grice, Martinez, GA (US)

(73) Assignee: HealthTronics Laboratory Solutions, Inc., Austin, TX (US)

( * ) Notice: Subject to any disclaimer, the term of this patent is extended or adjusted under 35 U.S.C. 154(b) by 0 days.

(21) Appl. No.: 11/648,279

(22) Filed: Dec. 29, 2006

(65) Prior Publication Data
US 2007/0183938 A1    Aug. 9, 2007

Related U.S. Application Data

(60) Provisional application No. 60/755,381, filed on Dec. 30, 2005, provisional application No. 60/801,486, filed on May 18, 2006.

(51) Int. Cl.
G01N 21/75    (2006.01)

(52) U.S. Cl. ......... 422/400; 600/562

(58) Field of Classification Search ......... 422/102; 600/562, 564
See application file for complete search history.

(56) References Cited

U.S. PATENT DOCUMENTS

| | | | |
|---|---|---|---|
| 5,061,452 A * | 10/1991 | Yamamoto et al. | 422/101 |
| 5,080,869 A * | 1/1992 | McCormick | 422/102 |
| 5,127,537 A | 7/1992 | Graham | |
| 5,424,040 A * | 6/1995 | Bjornsson | 422/101 |
| 5,752,234 A * | 5/1998 | Withers | 705/2 |
| 5,817,032 A * | 10/1998 | Williamson et al. | 600/562 |
| 5,928,934 A * | 7/1999 | McCormick | 435/284.1 |
| 6,258,327 B1 * | 7/2001 | Tatum | 422/102 |
| 6,518,542 B1 * | 2/2003 | Robertson et al. | 219/121.69 |
| 2002/0106626 A1 * | 8/2002 | Muraca | 435/1.3 |
| 2002/0127580 A1 * | 9/2002 | Quay | 435/6 |
| 2002/0162843 A1 | 11/2002 | Alley | |
| 2004/0019299 A1 | 1/2004 | Ritchart et al. | |
| 2004/0031721 A1 * | 2/2004 | Mann | 206/570 |
| 2007/0116612 A1 | 5/2007 | Williamson, IV | |
| 2007/0122797 A1 * | 5/2007 | De La Torre-Bueno | 435/4 |

OTHER PUBLICATIONS

Patent Cooperation Treaty, International Search report, International Application No. PCT/US2006/049515, mailed Oct. 15, 2007, 7 pages.
Written Opinion of the International Search Authority mailed Oct. 15, 2007 corresponding to Application No. PCT/US2006/049515.
Office Action mailed Jul. 1, 2009 for EP Application No. 06 846 087.2.

(Continued)

*Primary Examiner* — Max Hindenburg
*Assistant Examiner* — Renee Danega
(74) *Attorney, Agent, or Firm* — DLA Piper LLP (US)

(57) ABSTRACT

The present invention relates to a kit for taking biopsies, resections, excisions, and/or autopsies. Moreover, the present invention relates to methods of taking biopsies resections, excisions, and/or autopsies using the kit of the present invention. The kits and methods of the present invention allow for fewer errors, decreased turn around time and/or more rapid processing due to a cassette and specimen numbering system that is simplified and superior over that which has been previously disclosed in the prior art. The kit of the present invention comprises one or more tissue cassettes, and optionally one or more bottles of formalin and optionally, other components.

42 Claims, 1 Drawing Sheet

OTHER PUBLICATIONS

English translation of Office Action, Date of Issuing: May 12, 2011 corresponding to Chinese Patent Application No. 200680053582.3 in 9 pages.

Correspondence to counsel for Therapak Corp. from counsel for Assignee Claripath Laboratories, Inc. dated Jan. 19, 2010 regarding U.S. Appl. No. 11/648,279.

Correspondence from counsel for Therapak Corp. to counsel for Assignee Claripath Laboratories, Inc. received Feb. 8, 2010 regarding U.S. Appl. No. 11/648,279.

Office Action mailed Sep. 18, 2009 corresponding to Chinese Patent Application No. 200680053582.3.

Office Action mailed Oct. 23, 2009 corresponding to Chinese Patent Application No. 200680053582.3.

* cited by examiner

KIT FOR TAKING BIOPSIES, AUTOPSIES, EXCISIONS, AND RESECTIONS AND METHODS THEREOF

This application claims priority under 35 USC §119(e) to U.S. Provisional Application Nos. 60/755,381, filed Dec. 30, 2005, and 60/801,486, filed May 18, 2006 the entire contents of which are incorporated by reference.

BACKGROUND OF THE INVENTION

Tissue biopsies are a commonly employed technique for diagnosing diseases in any of a plurality of species such as in plants and other life forms like animals, particularly in humans. Biopsies can be taken to diagnose any of a plurality of diseases, at sites including but not limited to bone biopsies (for people with bone pain and other indicators of bone cancer/neoplasm), bone marrow biopsies (for people with an abnormal blood counts, such as unexplained anemia, high white cell count, and low platelet count), breast biopsies (to confirm if a lesion is benign or malignant), cervical biopsies (to diagnose cervical cancer/neoplasm or other cervical diseases), joint biopsies (where a tissue specimen is taken from synovial membrane that lines the joint to diagnose gout, pseudogout, bacterial infections, lupus, rheumatoid arthritis or Reiter's disease), kidney biopsies (to diagnose any of a plurality of disorders), liver biopsies (to identify liver disorders and diagnose abnormalities as benign or malignant), lymph node biopsies (to diagnose diseases such as chronic lymphatic leukemia, Hodgkin's disease, infectious mononucleosis, and rheumatoid arthritis), lymph node biopsies (to diagnose if cancer has spread from a primary location into the lymphatic system), lung biopsies (to diagnose a plurality of lung diseases or abnormalities such as cancer/neoplasm or other lung diseases), pleural biopsies (to diagnose malignant and non-malignant diseases and to diagnose viral, fungal, or parasitic diseases and collagen vascular diseases of the pleura (the sac covering the lungs)), prostate biopsies (to diagnose prostate cancer/neoplasm and/or to determine the cause of prostate enlargement or elevated, an abnormal percentage or an increasing value of serum prostate markers such as the prostate specific antigen (PSA)), small intestine biopsies (to diagnose the cause of diarrhea or poor absorption in the intestine), skin biopsies (to diagnose malignant cancer or benign neoplasm and/or chronic bacterial and/or fungal skin infections), synovial biopsies, and thyroid and/or parathyroid biopsies (to diagnose patients with thyroid enlargement and/or nodules, breathing and/or swallowing difficulties, vocal chord paralysis and/or other problems such as unexplainable weight loss).

Other biopsies that can be done include biopsies that can be done at body sites such as on the stomach, esophagus, oral cavity, pharynx, larynx, colon/rectum/anus, bladder, pancreas, spleen, central nervous system, peritoneum, genitalia and reproductive organs, heart, mediastinum, and many other sites. In addition to the reasons enumerated above for performing biopsies, any of numerous other diagnoses can be performed.

The method and the kit of the instant invention (which will be described in more detail below) are general and can be used in any of the above described biopsies (or even in biopsies that are not described above). The methods and kits of the present invention may be used for tissue biopsies, or alternatively, may be used for tissue excisions, resections, autopsies, for analyzing tissues and/or materials that are excreted and/or secreted by the patient, and tissues and/or materials that may be submitted by the patient or some other one or more entities. However, for the sake of understanding the invention, the invention will be described below with respect to a particular embodiment (i.e., prostate biopsies).

Cancer of the prostate is the most prevalent malignancy in adult males, excluding skin cancer, and is an increasingly prevalent health problem in the United States. In 1996, experts estimated that 41,400 deaths would result from this disease in the United States, indicating that prostate cancer is second only to lung cancer as the most common cause of death in the same population. The incidence of prostate cancer showed 230,110 new cases for prostate cancer in the United States in 2004. There were 975 new cases of prostate cancer per 100,000 men over 65 in the USA in the period from 1996-2000. Despite the large numbers of men affected by prostate cancer/neoplasm, if the cancer/neoplasm is diagnosed and treated early, when the cancer/neoplasm is still confined to the prostate, the chances of cure are relatively high.

Generally, diagnosis of prostate cancer/neoplasm involves detecting a relatively high level of PSA in a blood test and/or a digital rectal exam (DRE). If the level is at a level at which a physician thinks that a follow up biopsy is warranted, the physician may take a biopsy of the prostate gland. The prostate biopsy may show that the patient has BPH (benign prostatic hyperplasia) or perhaps a more serious malignant tumor.

BRIEF SUMMARY OF THE INVENTION

The present invention relates to a kit for taking biopsies, autopsies, resections, and/or excisions. Moreover, the present invention relates to methods of taking biopsies, autopsies, resections, and/or excisions using the kit of the present invention. The kits and methods of the present invention allow for fewer errors due to a cassette and specimen numbering system that is simplified (and thus, more elegant) over any system previously disclosed in the prior art. The kit of the present invention comprises one or more tissue cassettes, and optionally one or more bottles of formalin and optionally, other components.

BRIEF DESCRIPTION OF THE SEVERAL VIEWS OF THE DRAWING

The abbreviations used in the FIGURE are Left Base (LBase), Left Mid (LMid), Left Apex (LAPex), Left Lateral Base (LLatBase), Left Lateral Mid (LLatMid), Left Lateral Apex (LLatApex), Left Transition Zone (LTransition) (and the corresponding areas on the right side). FIG. 1 shows a 14 cassette kit, which may optionally be a 16 cassette box kit, which has the shown 14 cassettes plus two additional cassettes for a seminal vesicle sample on either side (it may be inserted before the transition zone cassettes).

DETAILED DESCRIPTION OF THE INVENTION

Figure 1:
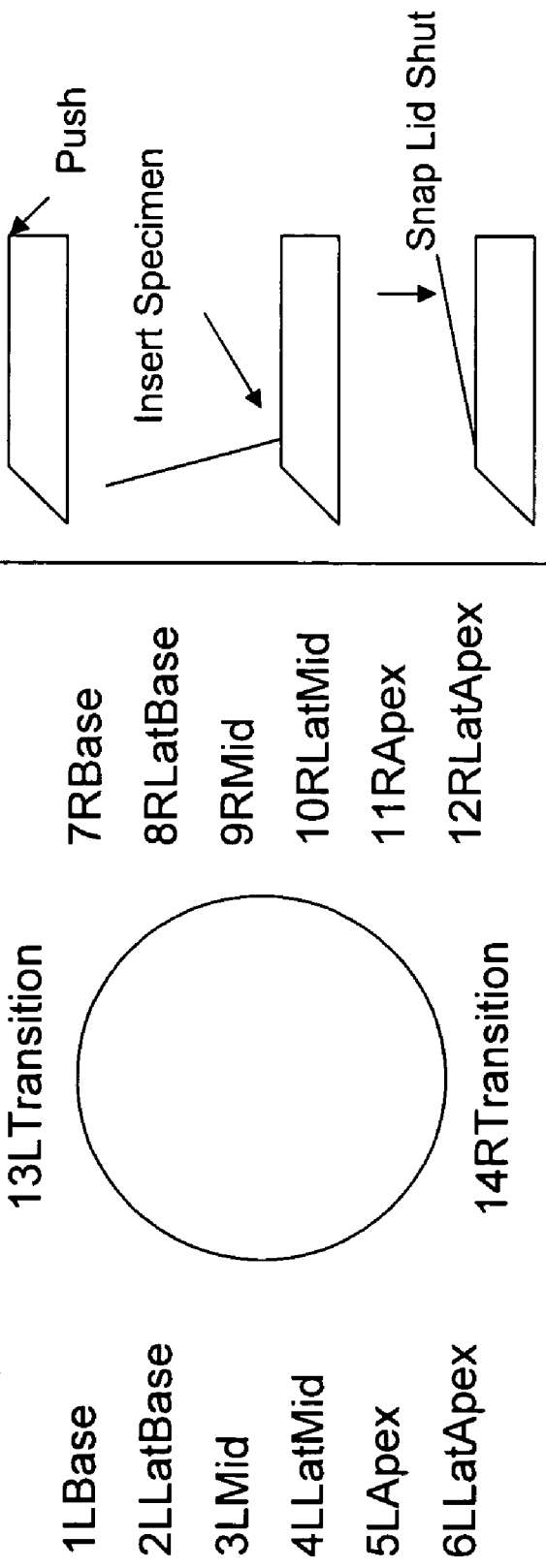
FIG. 1 shows a schematic of a kit, with 14 different sample areas to collect samples from the prostate, a top view of a bottle of formalin (or any of a number of other fixatives) and a side view of three tissue cassettes: the top cassette shown prior to opening it to insert the tissue sample (i.e., shut), the middle cassette shown open allowing for insertion of one of the 14 tissue samples, and the bottom cassette being closed after insertion of the sample.

It should be recognized that when the term cancer is used in the present invention, it is contemplated that any neoplasm is contemplated, whether it be a malignant cancer, a benign neoplasm or any neoplasm of uncertain malignant potential (UMP). It is also contemplated that lesions may be biopsied that are benign and non-neoplastic, such as infections, trauma, degenerative, metabolic and genetic lesions.

Generally, a prostate biopsy involves what is termed a core needle biopsy, wherein a tissue of sample from the prostate or another site such as the seminal vesicle of a patient is removed and then examined under a microscope. It should be understood that although the present invention is described by examining a biopsy sample using a microscope, other means of examination are contemplated such as digital whole slide imaging technologies, telepathology, and other related technologies (such as technologies wherein the microscopic image may be viewed on a videoscreen and/or remote microscope(s). Other means of examination may also include various types of tissue staining, (including routine staining (most commonly with hematoxylin and eosin but optionally with other stains), special staining (including numerous stains for tissue and cellular structures and components, proteins, nucleic acids, amyloid, carbohydrates, lipids, pigments, minerals, neuroendocrine structures, micro-organisms, bone, neuropathologic structures, and others), enzyme histochemical staining (including numerous stains such as immunostaining, stains related to or associated with a polymerase chain reaction (PCR), in situ polymerase chain reaction, in situ hybridization (ISH), fluorescence in situ hybridization (FISH), chromogenic in situ hybridization (CISH), staining for DNA or RNA content, staining for electron microscopy, and other special stains). The tissues may undergo numerous other studies including frozen sectioning, cytopathology, polarized light microscopy with or without slow wave compensation, spectral/multispectral analysis, darkfield microscopy, dissecting microscopy, microbiologic culture and other microbiologic studies, flow cytometry, cytogenetics, molecular pathology studies, electron microscopy, immunoelectron microscopy, immunogold labeling studies, qualitative or quantitative chemical analysis, ploidy/DNA content analysis by image analysis, image analysis for diagnosis of prognostic markers, histometry, mophometry, autoradiography, radioisotopic studies, nanotechnology studies, and other studies.

In the prostate embodiment, the physician inserts one or more narrow needles using any of a plurality of insertion points into the prostate gland. The insertion points for the needle include through the wall of the rectum (transrectal biopsy), through the urethra (transurethral biopsy), and/or through the perineum (transperineal biopsy). The needle may be guided to the prostate gland by using the physician's finger, by ultrasound, or by any other known invasive or non-invasive technique or combination thereof. The needle removes a cylinder of tissue that is about 1-1.5 centimeters in length and about 0.1-0.2 cm in diameter. Generally, a plurality of these cylinder samples of tissue will be taken at a plurality of locations from the prostate gland. Typically, anywhere from 6-20 cylindrical tissue samples are taken with 12-14 samples being common. Although a particular needle size is disclosed above, it should be recognized that any of a plurality of sized needles can be used. Moreover, a "saturation" biopsy may be performed wherein many more biopsies may be taken such that on the order of 40-80 samples (or more) may be taken. It should be understood, however that any number of samples may be taken.

For example, a urologist may use a grid to make sure many different locations are sampled. In some cases (such as when a previous biopsy shows atypia, a suspicious but not definitive diagnostic for malignancy in one particular location), the urologist may focus on that particular area only with saturation biopsies, so the number might be lower than 40 samples—for example, at least 4 biopsies, but usually many more.

The physician will then place this plurality of samples in a plurality of different vessels containing preservative and/or fixative for transport to a pathology lab where a pathologist and/or a laboratory technician will analyze the biopsies for possible cancer. The fixative may be present in the one or more cassettes before distribution to the physician or can be added at a later time (for example, when the physician is preparing the samples). A preservative and/or fixative commonly employed is formalin (which is aqueous formaldehyde and may optionally contain one or more alcohols (such as methanol), and/or formic acid). Other fixatives can be used such as various alcohols, methyl alcohol, ethyl alcohol, alcoholic zinc formalin, Bouin's Fixative, Carnoy's Fixative, Holland's Fixative, glutaraldehyde, B5 fixative, 95% Alcoholic Bouin's Fixative, 95% alcohol fixative, formalin fixative, acrolein, glyoxal, Karnovsky's Fixative (glutaraldehyde), Hartman's Fixative, Orth's Solution (dichromate fixative), Zenker's Fixative, acetic alcohol, Helly's, Michel's, Paraformaldehyde, osmium tetroxide, potassium permanganate, potassium dichromate, chromic acid, mercuric chloride, picric acid, combined reagents, carbodiimides, heat, microwaves, excluded volume fixation, vapor fixation, and many other types of fixatives. Alternatively, in some situations a fixative may not be used. In some situations, the specimen may be kept sterile. In some situations, a substance other than a traditional fixative may be used to preserve or to otherwise pre-treat the specimen (alternatively, other pretreatment methods may be employed). For example, the specimen may be placed in a saline solution which may or may not contain a preservative. In some situations a solution may be used, such as a balanced salt solution, a RPMI solution (Roswell Park Memorial Institute solution), cell culture media solution, or a microbiologic culture or transport media solution. A physician will generally label each of the vessels with identifying indicia, including but not limited to the patient's name (it may or may not be the patient's real name depending on whether the sample is sent in-house or to an external lab), the location of the sample taken, and/or other identifying indicia (such as a patient's accession number (to protect privacy)), etc.

Once the samples arrive at the pathology lab, the pathologist and/or the laboratory technician will take each of the biopsy core samples out of the vessels containing the preservative and/or fixative and transfer the samples to tissue cassettes. The tissue cassettes are then generally processed in a tissue processor that dehydrates the samples. The tissue processor exposes the cassette(s) containing the sample(s) to progressively more concentrated solutions of alcohols (with ethanol being an example of a commonly employed alcohol). Alcohol is applied to the cassettes in progressively greater concentrations to allow for slow dehydration so as to protect the tissue samples from damage. After a highly concentrated sample of alcohol is used (95% or greater), the sample may be exposed to acetone to further dehydrate the samples (ethanol typically forms an azeotrope with water and thus, getting very high concentrations of pure ethanol is difficult without co-distillation in benzene or some other suitable solvent).

After dehydration, the tissue samples may optionally be ready for "clearing". "Clearing" is placing the samples in a solvent to render the sample optically clear so that they can be viewed under a light microscope. A typical organic solvent that can be used in "clearing" is xylene. Other solvents are known to those of ordinary skill in the art that can be used for clearing (and these solvents are within the scope of the present invention). Although, the above sample preparation is described by using "clearing", it should be understood that this is an optional step that does not have to occur in all sample preparation. After, clearing, the samples are further processed by imbedding them in fluid paraffin wax (which is then cooled to generate solid paraffinic samples), which will allow the samples to be cut for viewing on slides. Xylene is typically used as a solvent because it provides a miscible interface between paraffin and ethanol (because paraffin and ethanol, in the absence of a co-solvent, are immiscible. Other methods for embedding are contemplated such as plastic and resin embedding. After tissue embedding the following steps may be performed—microtomy (slide cutting) and various types of tissue staining, (including routine staining (most commonly with hematoxylin and eosin but possibly with other stains), special staining (including numerous stains for tissue and cellular structures and components, proteins, nucleic acids, amyloids, carbohydrates, lipids, pigments, minerals, neuroendocrine structures, micro-organisms, bone, neuropathologic structures, and others), special histochemistry staining, enzyme histochemical staining, immunostaining, staining associated with the polymerase chain reaction (PCR), in situ polymerase chain reaction, in situ hybridization (ISH) staining, fluorescence in situ hybridization (FISH), chromogenic in situ hybridization (CISH), staining for DNA or RNA content, staining for electron microscopy, and other special stains). The tissues may undergo numerous other studies including frozen sectioning, cytopathology, polarized light microscopy with or without slow wave compensation, spectral/multispectral analysis, darkfield microscopy, dissecting microscopy, microbiologic culture and other microbiologic studies, flow cytometry, cytogenetics, molecular pathology studies, electron microscopy, immunoelectron microscopy, immunogold labeling studies, qualitative or quantitative chemical analysis, ploidy/DNA content analysis by image analysis, image analysis for diagnosis of prognostic markers, whole slide imaging, telepathology, histometry, mophometry, autoradiography, radioisotopic studies, nanotechnology studies, and other studies.

Although tissue cassettes are described above, it should be recognized that any of a plurality of different cassettes can be used such as for example, different types of cassettes other than the ones that are described above. Examples of cassettes include self-embedding cassettes in which the tissue can be left in the same compartment in which it was processed and embedded there, wherein the self-embedding takes place by pushing the sample(s) out of the front or back of the cassette using a telescoping lattice of thin plastic. Other types of cassettes are also contemplated and within the scope of the present invention. For example, larger or multi-specimen cassettes that are capable of holding multiple biopsies in different wells or multiple detachable cassettes are contemplated. Thus, in one embodiment, the cassettes may contain a plurality of wells for a plurality of different tissue samples.

In an embodiment, the cassettes may contain no fixative or other substance at the time of distribution to the physician. In another embodiment, the cassettes may contain fixative or other substances at the time of distribution to the physician, or alternatively, the cassettes may have fixative or other substances added to them at a later time (as opposed to the cassettes being placed into fixative or other substance). In a variation of this embodiment, the tissue cassettes may be developed with different methods for placing tissue inside, for example by injection of the tissue or by pushing the tissue through a self-sealing membrane. This cassette type may include labels indicating the body sites from where the biopsy is to be collected or from where the biopsy is collected (i.e., the biopsy site can be predetermined or determined later).

The kit of the present invention may contain any of these above described cassettes. Moreover, the kit may contain any of a plurality of different cassettes and/or different cassette types.

Any of a plurality of different methods can be used for inserting biopsies into cassettes—such as by ejecting from a biopsy device, placing the sample on a sponge/paper/tissue/agar/gelatin or other materials which may be placed into the cassette or left outside. Any of a plurality of devices such as sticks, blades, or squirt bottles (within or separate from the biopsy kit) can be used to assist in removal. All of these above described devices may optionally be included in the kit. Biopsy devices (needles, handles, and other tools) may be included in the kit or perhaps can be procured separately. Instructions for using the kit, mailing labels, labels indicating biopsy sites and other information about the biopsies, and other information, including info about the lab may be included in the kit or perhaps may be procured separately.

Pathology labs may prepare and perform hundreds or thousands of sample preparations per day with a plurality of patients, a plurality of different types of samples (from many biopsies or autopsies), and a plurality of different locations for each of the biopsies. Thus, during sample preparation, there is the potential for errors resulting from sample mix-ups. Moreover, the preparation of samples and particularly, the transfer of tissue samples from formalin to cassettes can lead to a plurality of other possible errors such as destroying the samples due to crushing the samples, an inability to locate the samples because they are stuck on the formalin vessel (or not present at all in the formalin), dropping the samples during transfer (leading to contamination), placing the samples in the wrong cassette (such as placing a sample from a different site into the wrong cassette or the sample from a different patient into the wrong cassette), or any other of a plurality of other errors that arise out of the transfer of samples from the formalin to the cassette. Further, the transfer of samples from formalin to a tissue cassette requires time, which leads to greater expense (particularly if the transfer is performed by a well-paid pathologist) that is usually placed upon the patient. The time that it takes to transfer samples from formalin to cassettes is time that could be used by the pathologist or laboratory technician to correctly analyze samples. If the pathologist or laboratory technician has to transfer samples from formalin to cassettes, this may lead to longer delays in receiving results or possibly inaccurate readings due to less time available to analyze samples (leading to slower diagnosis and potentially, greater danger to patients because of mis-readings.

Thus, an object of the instant invention is to reduce the possibility of errors in the transfer of tissue samples from formalin to cassettes and to reduce the drawbacks associated therewith.

Thus, in an embodiment, the present invention relates to a kit for taking biopsies and/or for sampling other samples such as resections, excisions, etc. The tissue kit of the present invention can be used for any of biopsies, resections, excisions, and/or autopsies. In one embodiment, the tissue kit contains one or more cassettes. In another embodiment of the present invention, the kit is all-inclusive so that no instruments and or solvents are required more than what is in the kit. Moreover, the present invention relates to methods of taking biopsies using the kit of the present invention. The kit of the present invention comprises one or more tissue cassettes, and optionally one or more bottles of formalin, and optionally, other components.

In a further embodiment, the present invention also relates to business models for delivering and handling tissues using the kit of the present invention. For example, the tissues can be processed in route to a lab (for example, in a vehicle) or in a site remote from a physician or technician (for example, a pathologist), and the present invention also allows whole slide images or other methods of telepathology to be used to transport the diagnostic images to pathologists. Moreover, the tissue sectioning and staining may be done in the same way.

In an embodiment, the present invention relates to a biopsy kit that has components that have not previously been in biopsy kits. A laboratory or a hospital that is in the business of doing anatomic pathology will receive biopsy, excision, resection, and autopsy specimens, such as prostate biopsies, from all over the world. Thus, although the invention is not limited to prostate biopsies, to understand the invention, the instant invention has been and will be described with reference to a prostate biopsy. Accordingly, the description of a biopsy is not to be limited to only prostate biopsies, but to include other biopsy, autopsy, excision, and resection procedures. For example, the biopsies that can be done include but are not limited to bone biopsies, bone marrow biopsies, cervical biopsies, joint biopsies, kidney biopsies, liver biopsies, lymph node biopsies, lung biopsies, pleural biopsies, prostate biopsies, small intestine biopsies, skin biopsies, synovial biopsies, thyroid and/or parathyroid biopsies and other biopsy procedures.

In an embodiment, a physician who is a urologist will do 12 or 14 needle core biopsies from specified locations in the prostate gland. A needle core biopsy generally is a biopsy that is done using a long needle wherein the physician (e.g., urologist) goes through one or more of the wall of the rectum (transrectal biopsy), the urethra (transurethral biopsy), and/or the perineum, which is the region bounded dorsally by the pubic arch, ventrally by the coccyx, and laterally by part of the hipbone (transperineal biopsy). The physician inserts the needle so that cylindrical tissue samples are removed from the prostate that are about 1-1.5 centimeters in length and about 0.1-0.2 cm in diameter (although it is contemplated that any of a variety of sizes of needle sizes can be used). It should be understood that although the invention is described with reference to taking samples by use of a needle other means of taking samples are contemplated and are within the scope of the present invention. In an embodiment, the kit of the present invention may contain a plurality of bottles of formalin into which the cylindrical tissue samples are put. Optionally the kit may have tissue cassettes.

Thus, in an embodiment, the present invention is a tissue kit that contains one or more tissue cassettes. Instead of placing the cylindrical tissue samples that are withdrawn from different regions in the prostate into separate formalin bottles, the physician might instead place the cylindrical tissue samples that are withdrawn from different regions in the prostate into tissue cassettes. One advantage of placing the cylindrical tissue samples that are withdrawn from different regions in the prostate into tissue cassettes is that a step may be omitted. This means that less work is done by the combination of the urologist (who takes biopsy samples from patients) and from the pathologist and/or lab technician (who traditionally would perform the task of transferring the cylindrical tissue samples that are withdrawn from different regions in the prostate from formalin bottles to a place where tissue samples might be analyzed, and then subsequently, analyze the samples).

Another advantage to having the urologist directly put the cylindrical tissue samples that are withdrawn from different regions in the prostate into tissue cassettes is that the chance of sample mix-ups is reduced because a urologist generally will remove the biopsy sample and immediately put that biopsy sample into a cassette that has identifying indicia attached to the tissue cassette. In kits currently used, two transfers are done, the urologist places the biopsy sample into one of a plurality of formalin vessels and sends the samples to a lab where a laboratory technician or pathologist transfers the biopsy sample to tissue cassettes. Using this method, the tissue cassettes have to have the same identifying indicia as each of the corresponding formalin vessels. Having two transfers leads to errors. By having only one transfer (i.e., from the prostate directly to the tissue cassette), the possibility of errors is greatly decreased. Moreover, if the urologist (in the doctor's office while seeing a patient) does the transfer instead of a lab technician or pathologist in a lab that handles a plurality of samples, there is only one patient who is having biopsies sampled and the chances of sample mix-ups with other patients' biopsies is decreased.

Further, by having the urologist do the initial placement of the biopsy sample into the tissue cassette, the additional transfer step (from the formalin vessel to the tissue cassette) is not needed, which should save both time and money. Faster diagnoses can be done, which aids in the more rapid initiation of therapies and also may aid in the reduction of patient anxiety. The time savings can also be used for other purposes such as analyzing the tissue sample by the pathologist or the lab technician. The savings in money is a result of the fact that time is not needed to be spent on the additional transfer step.

In an embodiment of the invention, the tissue cassettes have identifying indicia associated with them. The identifying indicia may include such things as the patient name, patient accession number, location on a body where a biopsy is to be performed, a human readable body site (such as LBase), business address information, hospital address information, social security number information, patient medical history information, date information and time information as well as other identifying indicia.

The patient name may or may not be associated with the tissue cassette. If the samples are to stay in house (at the hospital) wherein patient confidentiality is not a concern, the tissue cassettes may have a name associated with them. In contrast, if the sample is to be sent to an external lab where patient confidentiality is at issue, the tissue cassettes may not have a name associated with them. Instead, a patient accession number may used that identifies only the patient by a number that the urologist can later match to the patient.

The tissue cassettes may also have locations of the body from where the tissue is sampled. For example, when a biopsy is taken from a prostate, samples are taken from a plurality of locations as tumors may be localized in only one area. Sampling from a plurality of areas increases the likelihood that a tumor will be located. It is acknowledged that false negatives still may occur if the samples are not obtained from an area where a tumor is located. However, the likelihood of locating a tumor that is present is increased by increasing the number of samples from different regions of the prostate. An example of how the cassettes may be labeled is to label the cassettes with the following 14 locations (as shown in FIG. 1): 1) LBase, 2) LLatBase, 3) LMid, 4) LlatMid, 5) LApex, 6) LLatApex, 7) RBase, 8) RLatBase, 9) RMid, 10) RLatMid, 11) RApex, 12) RlatApex, 13) Ltransition and 14) R Transition. The urologist will know to place the sample that is obtained from the left base of the prostate into the cassette that is cassette number 1). The urologist will then subsequently collect samples from the other 13 locations and insert them into the correct cassette. The cassettes are then ready for further processing (e.g., placing them in formalin and eventually analyzing the samples). It should be understood, however, that the cassettes may already contain formalin or some other fixative in them when the samples are placed in the cassettes.

The kits can be designed in such a way so that the tissue may be facilely placed in the cassettes in any of a(n) Operating Room/Clinic/Office or other location by any of a submitting physician, by staff, by a pathologist, and/or by an assistant in any of the above enumerated locations.

In the kit of the present invention, there may also be one or more vessels of formalin although it is contemplated and therefore within the scope of the invention that no vessels of formalin are present. If a vessel of formalin is present (which may optionally be made a part of the kit), after the samples are collected, they can all be placed in this one formalin vessel for transfer to the lab where the pathologist and/or lab technician will further process the biopsy samples. Alternatively, fixative may already be present in the tissue cassettes when the tissue samples are placed in the tissue cassettes. It is also possible to have multiple bottles of formalin wherein each of the tissue cassettes containing the biopsy samples can be placed in their own bottle, or alternatively, a plurality of tissue cassettes can be placed in a bottle. For example, all of the samples that are collected from the left side of the prostate may be placed in one formalin vessel and all of the samples that are collected from the right side of the prostate may be placed in a different vessel of formalin. Other possible distributions of samples in formalin are possible and are contemplated as being part of the invention (for example, one tissue cassette per formalin bottle or all tissue cassettes in one bottle). Alternatively, as described above, the fixative may be in the cassettes itself. Alternatively, another substance (other than or in addition to a fixative) may be used.

The tissue cassettes may have the identifying indicia present in any number of forms or combinations thereof. These identifying indicia forms include but are not limited to having the identifying indicia present as alphanumeric characters so that they can be read by the physicians and/or lab technicians, and/or others, having the identifying indicia present as bar codes (in two or more dimensions) that contain the requisite information that can be read by a bar code reader, radio frequency detectors that can be read by a radio frequency detector reader, magnetic strips that can be read by a magnetic strip reader, or other known means of associating identifying indicia to objects, which can be read by optical or another type of scanner.

The alphanumeric characters may be in a code that has other identifying information associated with it. The alphanumeric characters of the present invention include not only alphabet letters and Arabic numerals, but also include all other letter and/or symbols, including but not limited to a hexadecimal system and the letters, numbers and symbols from other languages. In an exemplary embodiment of the present invention, a patient may have an accession number 1000. The cassettes would be labeled 1000-1, 1000-2, 1000-3, etc. where the first number (i.e., "1000") is associated with a patient that has further information associated with it and the second number is the place from where the biopsy was taken. (e.g., "1" may refer to the Left Base of the prostate).

Alternatively, the identifying indicia may be associated with the one or more vessels containing formalin (if there is formalin in the kit). There are advantages to having a plurality of tissue cassettes and one or only a few formalin vessels. One advantage is that if one has only one bottle of formalin, one need only label that one bottle of formalin as opposed to the 12 to 14 cassettes (or as with previous kits, the 12-14 bottles of formalin). This will save a urologist time. It should be understood that the cassettes may have been prelabeled with information such as the location from where the biopsy was taken. A second advantage of having a limited number of formalin bottles is that the formalin and the vessel in which the formalin resides tend to be more expensive than tissue cassettes (and also substantially larger in size). Thus, reducing the number of vessels and the amount of formalin means that the kit can be manufactured more inexpensively, the kit can be smaller and lighter and all associated costs can be reduced (such as mailing or shipping costs). For example, instead of having 14 vials containing 20 ml of formalin in each vial (i.e., 280 ml total of formalin), a single vial containing 200 ml of formalin can be used to accommodate the 14 tissue cassettes, or alternatively, two vials containing 100 ml of formalin can accommodate 7 tissue cassettes each. A smaller and lighter kit means that costs associated with transport is less. Alternatively, the kit of the present invention may have fixative or other substance that is already within tissue cassettes or may be added at a later time. This kit may be advantageous in that it may be even smaller and more convenient than the kit that contains fixative or other substance not in the cassettes.

The kit may optionally have other components associated with it in addition to the one or more tissue cassettes and the one or more vessels of formalin. These components include but are not limited to: needles or other devices for taking biopsies (such as a biopsy handle), solvents to further process the biopsy samples, absorbent pads, plastic bags to send/receive the kit (e.g., biohazard safe plastic bags), agar, gelatin, filter paper, sponges, blades, sticks squirt bottles, materials for orienting and marking margins/locations with ink, written or diagrammatic instructions on how to perform the biopsy including information as to where to collect samples, where to send the samples, how to pack the samples, etc., additional tissue cassettes, absorbent pads on which to place the tissue cassettes while collecting or processing samples, corrugated cardboard for cushioning the samples during transport or during sample preparation, self adhesive labels that can be attached to the tissue cassettes, shipping labels and other components.

In one embodiment, the cassettes have pre-assigned numbers, which allow the slides and blocks to be archived as follows. Because the cassettes have pre-assigned numbers the cassettes may be received out of sequence. Conventionally, labs may have stored slides and/or blocks sequentially by accession number. The present invention allows one to store the slides and/or blocks sequentially, however, storing the slides and/or blocks sequentially might require large empty spaces between accession numbers in the system to accommodate the slides and/or blocks with accession numbers that are to sequentially fill in these spaces. Moreover, the lab may also not know how much space to leave for the slides and/or blocks as it would be unknown as to when the slides and/or blocks may be received. In this case, slides and/or blocks with lower accession numbers may arrive from clients much later than higher accession numbers on slides and/or blocks from other clients. One means of addressing these drawbacks is to store slides in blocks in one or more boxes or some other appropriate compartment. The blocks (or compartment) may be numbered or may contain some other means of identification (such as bar codes, RF chips that have identifying indicia associated with them). The one or more boxes may contain one or more drawers. When the slides and/or blocks are stored, the box year, box number, and drawer number or other appropriately identifying features are entered into a laboratory information system (LIS). Entering the identifying features in one embodiment is done automatically by using RFID technology, and in alternate embodiments may be done by using a scanner for bar codes or alternatively may be entered manually by an operator. If one ever needs to retrieve the materials inserted into the boxes, the information may be looked up under any of the identifying features such as under that patient's name (or other patient identifying feature) that is in the LIS.

It is contemplated and therefore within the scope of the invention that should the slides and/or blocks be stored sequentially, an automated system might be employed that does not require that space be left between the slides and/or blocks to accommodate slides and/or blocks that are incoming. Rather, when new slides and/or blocks arrive, the newly arriving slides and/or blocks are scanned (using bar code or RFID technology) and a computer system instructs the newly arriving slides and/or blocks where to go. In an embodiment, conveyor belts and/or rollers may be used to position the slides and/or blocks into the correct sequential location. It is contemplated that these slides and/or rollers may be in two dimensions or alternatively, in three dimensions (with three dimensions being preferred as space is used more efficiently). In this embodiment, the slides and/or blocks that previously were in place (such as those that are being stored) will also be moved by the conveyor belts and/or roller systems to make space for the newly arriving slides and/or blocks.

In an embodiment, the kits may be received in non-sequential order with regards to the accession numbers, so that the kits can be archived by date. In a variation of this embodiment, the different specimen data may be archived by date, by accession sequence, by the submitting or referring physician, or by other data or metadata stored with the specimen. Alternatively, human readable information may be used, such as bar codes (linear, 2 dimensional, etc.), RFIDs, or other technologies for identifying cassettes, blocks, slides, requisition forms, reports, and other tangible objects related to the patient and specimen(s). In this variation of the embodiment, this is basically a cassette and specimen numbering system.

In an embodiment, the kit concept of the present invention may be adapted for more generic use. In this embodiment, prelabeled cassette kits may contain any number of cassettes with the same number and with different prefixes (or alternatively, different suffixes) for the accession number. These different prefixes (or suffixes) allow one to assign different accession sequences in the LIS. In this embodiment, a patient (or a group of patients or a given lab with multiple patients) with multiple specimens on the same day may have different kits with different accession number that can be linked together. In other words, a specimen received on the same day from the same procedure can be linked together in the LIS so that the results are reported together in a single report, or separated into different reports, depending on the desires of the particular lab. In this embodiment, the accession prefix/different accession sequence allows one to automatically create a report template for predefined specimen types, such as with prostate samples. In a particular variation, a "GIG" prefix might indicate a gastric biopsy, generating a standard, partly completed pathology report with default values. The prefix may trigger certain additional future events to occur such as (a) special stain(s) may be automatically ordered. Alternatively, a "GIC" prefix might indicate a colon biopsy, which also might trigger future events to occur. Alternatively, the cassettes may include accession/internal lab numbers with different prefixes identifying accession sequences which in turn identify specimen types. In this embodiment, this procedure can be used to automatically generate a report that fits the kit type. By using this methodology, the kit and methods using the kit generates time and money savings in a lab. A variation on this embodiment allows other events to be triggered such as automatically printing appropriate slide labels (thus, instructing the technologists in how many levels to cut). Moreover, the kit may include slides labeled with special stains, controls, etc., which are predetermined by protocol.

It is possible that a single kit may contain cassettes with different lab identification numbers/codes. It may be possible for such kits to generate more than one report, possibly created by different pathologists. For example, a urologist might send a kit with 2 bladder biopsies and 1 skin biopsy. In some labs, all will be signed out by the same pathologist on the same report; in others the bladder biopsies will be signed out on a report by a uropathologist and the skin biopsy by a dermatopathologist on a different report. Other information systems, such as electronic healthcare systems, may have the capacity to combine or separate these different report types for a variety of reasons, including administrative, billing, research, teaching, and patient confidentiality. Lab data may be incorporated into the EHR (electronic health record) within institutions and even in wider networks. Thus, in an embodiment, the present invention allows for breaking down some things into component parts and presenting them in different views appropriate for different users, as well as preserving a report regarded as the authenticated "medicolegal" report document. The date/time received, patient ID, and other data can be used to link the specimens rather than the "accession" or lab number if they need to be combined in a pathology report or later in an EMR system. In this embodiment, the individual specimen (separately identified/identifiable) may be the atomic unit, so the individual specimen number together with other patient data can be used to replace the accession number. Thus, in an embodiment, the present invention relates to methods for utilizing the assigned specimen numbers and sub-numbers (like prefixes/accession sequences, block numbers, slide numbers, slide levels, special stains, etc.). The specimen number (specific for a particular type of specimen, which may be part of the number or in a prefix or suffix number associated with the sample) may also identify information pertaining to subparts of the specimen; for example, if a uterus is received, it may automatically generate slide labels and reports for a standard uterus report.

An abbreviated generalized procedure for collecting the samples is as follows. The formalin container is labeled with the patient information using any of the labeling means discussed above. The correct tissue cassette is selected by the physician (e.g., urologist) for the corresponding biopsy location. The following can be understood with reference to the side images of the three cassettes that are shown in FIG. 1. The cassette lid may optionally be opened and the biopsy sample may be ejected or placed into the cassette. Alternatively, one may use a stick or a blade, or roll onto a pad, filter paper, or cassette surface. The lid can be used as a backstop when ejecting/placing the sample in the cassette, if needed. The sample may be optionally rinsed off. The cassette lid may be snapped shut (as shown in FIG. 1, the physician should insure that the lid is completely clicked shut). The cassettes are placed into one or more formalin vessels/containers as described above. Alternatively, the cassettes may already contain fixative or some other appropriate substance in them when the tissue samples are inserted into the cassettes. When all of the tissue cassettes have been placed in the one or more formalin vessels/containers, the lids for the one or more formalin containers are tightly closed and prepared for transport. The kit is also closed and placed in a box and/or bag for transport and the appropriate shipping labels are attached. The kit is sent to a lab for tissue processing and analyzing.

Tissue processing and preparation is as disclosed above.

Thus, the invention in one embodiment is directed to a biopsy kit comprising one or more tissue cassettes and optionally, one or more vessels containing a fixative and/or preservative. The kit may optionally contain a paper requisition form with accession numbers and/or other data identical or consistent with those on the cassettes in human readable, bar code and/or any other form. Labels may also be supplied for the fixative container with the same information. The kit may also provide online requisition capability or some other electronic communication requisition capability Such capability may have additional advantages such as notifying the laboratory of a specimen in transit for tracking and replying to the submitting physician's office when the kit has been received and other information, such as estimated reporting date/time.

In an embodiment, the fixative and/or preservative is formalin (or any of the fixatives disclosed above).

In an embodiment, the kit further comprises one or more thin needles for taking biopsies. In a further embodiment, the kit contains more than one thin needle.

In an embodiment, the tissue cassettes in the kit number from 1 to 20 or from 6 to 20. In another embodiment, the tissue cassettes in the kit number from 2 to 16 or from 2 to 14.

In an embodiment, the one or more tissue cassettes in the kit have identifying indicia associated with the tissue cassettes. In another embodiment, the identifying indicia is present in a form as one or more members selected from the group consisting of a bar code, a radio frequency device, and alphanumeric characters.

In another embodiment, the identifying indicia contains information regarding one or more members selected from the group consisting of patient name, patient accession number, location on a body where a biopsy is to be performed, business address information, hospital address information, social security number information, patient medical history information, date or time information (like date of birth or date and/or time sample was prepared, etc.).

In an embodiment, the kit further optionally comprises organic solvents for dehydrating and/or clearing tissue samples. In another embodiment, the organic solvents are a series of solutions containing different amounts of ethanol. In another embodiment, the kit further comprises an organic solvent that is xylene.

In another embodiment, the kit has instructions for performing biopsies.

The tissue kit of the present invention can also be combined with one or more other tissue kits. For example, in an embodiment, one tissue kit may be used that has green cassettes and combined with a tissue kit that has red cassettes. The combined tissue kits may be used to sample different biopsy regions or may be an indication that the tissue sample is to be treated differently. For example, if the tissue samples are from the same patient, the tissue samples in the green cassettes may undergo fixative treatment with one type of fixative and the tissue samples in the red cassettes may be treated differently. The different cassettes may also have different means of identifying indicia associated with them. For example, the green cassettes may have a bar code or an RF chip associated with them that contains certain identifying indicia whereas the red cassettes may have words or some other means of determining the identifying indicia associated with them.

Moreover, the present invention relates to a method of preparing samples for a biopsy comprising
a) taking core needle tissue samples and inserting the core needle tissue samples directly into one or more tissue cassettes,
b) inserting the tissue cassettes containing the core needle tissue samples into formalin,
c) exchanging the formalin with varying concentrations of a dehydrating solution to generate dehydrated core needle tissue samples, and
d) clearing the dehydrated core needle tissue samples with xylene.

In an embodiment, the method further comprises imbedding the dehydrated core needle tissue samples in fluid paraffin wax. In an embodiment, the method further comprises analyzing the dehydrated core needle tissue samples in fluid paraffin wax under a light microscope.

In an embodiment, the dehydrating solution contains ethanol. In an embodiment, the dehydrating solution contains acetone.

In an embodiment, the samples are from a prostate biopsy.

In an embodiment, the tissue cassettes contain pre-accession identifying indicia.

It should be understood that a plurality of elements have been disclosed above. It is contemplated and therefore within the scope of the invention that any one or more of these elements can be combined with any one or more elements disclosed above. It should be apparent to those of ordinary skill in the art that minor modifications can be made to any embodiment of invention without departing from the spirit and scope of the invention. Moreover, the invention is not to be limited by the disclosure above but is rather to be defined by the below claims.

I claim:

1. A tissue kit for receiving prostate biopsies that facilitates efficient histological processing of the tissue samples, the tissue kit comprising:
a plurality of tissue cassettes configured to receive tissue samples directly from at least one biopsy device used by a physician to obtain tissue samples from a prostate gland of a patient, wherein the plurality of tissue cassettes comprises at least twelve tissue cassettes, the plurality of tissue cassettes are adapted to retain the tissue samples during transport and during histological processing of the tissue samples, each of the plurality of tissue cassettes has a bottom portion and a top portion, the bottom portion defines at least one tissue receiving well and houses a tissue receiving material, the tissue receiving material comprises a sponge material, the top portion forms a lid to the bottom portion, the top portion is pivotably coupled to the bottom portion and is movable between a first closed position and a second open position, the top portion is releasably coupled to the bottom portion in a snap fit configuration in the first closed position, the bottom portion and the top portion each comprise a plurality of openings wherein the openings are small enough to contain the tissue sample within the tissue cassette during transport and during histological processing, but large enough to allow for a fluid to enter the tissue cassette during transport and during histological processing, wherein the plurality of tissue cassettes contain no fixative at the time of distribution to the physician, wherein the plurality of tissue cassettes include pre-assigned identifying indicia, wherein the pre-assigned identifying indicia comprise human readable alphanumeric characters indicating the body sites from where the prostate biopsy tissue samples are to be collected, wherein each tissue cassette corresponds to a single body site in that each of the tissue cassettes comprises a unique combination of human readable alphanumeric characters describing a unique prostate gland location to be sampled, the unique combinations of human readable alphanumeric characters are pre-assigned and marked on the plurality of tissue cassettes of the tissue kit prior to use of the tissue kit such that when each prostate gland tissue sample is collected by the physician the tissue sample is placed directly into the tissue cassette marked with the unique pre-assigned identifying indicia that corresponds to the unique single body site from which the tissue sample was taken; and at least one vessel containing a fixative, wherein the fixative comprises formalin, the at least one vessel comprises a first vessel having a size and configuration sufficient to hold at least half of the plurality of tissue cassettes of the tissue kit after the tissue samples have been placed directly into the plurality of tissue cassettes, wherein the amount of fixative within the first vessel is less than 280 ml but is sufficient to preserve the tissue samples retained within the at least half of the plurality of tissue cassettes when the tissue cassettes are positioned within the first vessel prior to histological processing.

2. The tissue kit of claim 1, wherein the identifying indicia comprise a bar code.

3. The tissue kit of claim 1, wherein at least a portion of the identifying indicia is associated with a patient.

4. The tissue kit of claim 1, wherein at least a portion of the identifying indicia is associated with a pathology accession number.

5. The tissue kit of claim 1, wherein a first cassette comprises a first color and a second cassette comprises a second color, the second color being different from the first color.

6. The tissue kit of claim 1, wherein the at least one vessel further comprises a second vessel having a size and configuration sufficient to hold at least half of the plurality of tissue cassettes of the tissue kit after the tissue samples have been placed directly into the plurality of tissue cassettes, wherein an amount of fixative within the second vessel is less than 280 ml but is sufficient to preserve the tissue samples retained within the at least half of the plurality of tissue cassettes when the tissue cassettes are positioned within the second vessel prior to histological processing.

7. A method of using a tissue kit for preparing tissue samples for a biopsy, a resection, an excision and/or an autopsy analysis of a prostate, the method comprising:

a) providing a tissue kit comprising a plurality of tissue cassettes and at least one vessel containing a fixative, wherein the plurality of tissue cassettes comprises at least twelve tissue cassettes and the at least one vessel comprises at least a first vessel, the plurality of tissue cassettes are adapted to retain the tissue samples during transport and during histological processing of the tissue samples, each of the plurality of tissue cassettes has a bottom portion and a top portion, the bottom portion defines at least one tissue receiving well, the top portion forms a lid to the bottom portion, the top portion is pivotably coupled to the bottom portion and is movable between a first closed position and a second open position, the bottom portion and the top portion each comprise a plurality of openings, wherein the plurality of tissue cassettes contain no fixative at the time of distribution to the physician;

b) taking tissue samples and inserting the tissue samples directly into one or more of the plurality of tissue cassettes, wherein the plurality of tissue cassettes include pre-assigned identifying indicia, wherein each tissue cassette corresponds to a single body site, wherein the pre-assigned identifying indicia comprise human readable characters indicating the body sites from where the tissue samples are to be collected, wherein a plurality of human readable characters uniquely describing the different locations to be sampled are pre-assigned and marked on each of the plurality of tissue cassettes of the tissue kit prior to use of the tissue kit, such that the source of each tissue sample placed directly into each of the plurality of tissue cassettes of the tissue kit corresponds to the pre-assigned identifying indicia indicating the body site marked on each of the plurality of tissue cassettes; and c) placing at least half of the plurality of tissue cassettes containing tissue samples into the first vessel containing the fixative, wherein the amount of fixative within the first vessel is less than 280 ml but is sufficient to preserve the tissue samples retained within the at least half of the plurality of tissue cassettes when the tissue cassettes are positioned within the first vessel prior to histological processing.

8. The method of claim 7, wherein the identifying indicia comprise a bar code.

9. The method of claim 7, further comprising associating at least a portion of the identifying indicia with a patient.

10. The method of claim 7, further comprising associating at least a portion of the identifying indicia with a pathology accession number.

11. The method of claim 7, wherein a first cassette comprises a first color and a second cassette comprises a second color, the second color being different from the first color.

12. The method of claim 7, wherein the at least one vessel further comprises a second vessel containing a fixative, the method further comprising placing at least half of the plurality of tissue cassettes containing tissue samples into the second vessel containing the fixative, wherein the amount of fixative within the second vessel is less than 280 ml but is sufficient to preserve the tissue samples retained within the at least half of the plurality of tissue cassettes when the tissue cassettes are positioned within the second vessel prior to histological processing.

13. A method of processing a tissue kit including one or more tissue samples for a prostate biopsy, the method comprising:

receiving a tissue kit comprising a plurality of tissue cassettes with tissue samples and at least one vessel containing a fixative, the plurality of tissue cassettes are adapted to retain the tissue samples during transport and during histological processing of the tissue samples, each of the plurality of tissue cassettes has a bottom portion and a top portion, the bottom portion defines at least one tissue receiving well, the top portion forms a lid to the bottom portion, the top portion is pivotably coupled to the bottom portion and is movable between a first closed position and a second open position, the bottom portion and the top portion each comprise a plurality of openings, wherein the plurality of tissue cassettes include pre-assigned identifying indicia, wherein the pre-assigned identifying indicia comprise human readable characters indicating a body location corresponding to a source of a tissue sample placed directly into each of the tissue cassettes, wherein each tissue cassette corresponds to a single body site, wherein a plurality of human readable characters uniquely describing different body locations are pre-assigned and marked on each of the plurality of tissue cassettes of the tissue kit prior to use of the tissue kit, wherein a tissue sample taken from a particular body location is in the tissue cassette marked with the pre-assigned identifying indicia corresponding to that particular body location, and wherein the plurality of tissue cassettes when received are positioned within the at least one vessel containing the fixative, wherein the at least one vessel comprises at least a first vessel, and wherein multiple tissue cassettes containing tissue samples are in the first vessel within the fixative; and exchanging the fixative with varying concentrations of a dehydrating solution to generate dehydrated tissue samples while maintaining the tissue samples within the plurality of tissue cassettes.

14. The method of claim 13, further comprising clearing the dehydrated tissue samples.

15. The method of claim 13, further comprising imbedding the dehydrated tissue samples in paraffin wax, plastic or resin.

16. The method of claim 13, further comprising archiving one or more tissue samples.

17. The method of claim 13, further comprising staining one or more tissue samples.

18. The method of claim 13, further comprising analyzing one or more tissue samples.

19. A tissue kit for taking prostate biopsies that facilitates efficient histological processing of the tissue samples, the tissue kit comprising:

a plurality of tissue cassettes configured to receive tissue samples directly from a prostate gland of a patient, the plurality of tissue cassettes are adapted to retain the tissue samples during transport and during histological processing of the tissue samples, each of the plurality of tissue cassettes has a bottom portion and a top portion, the bottom portion defines at least one tissue receiving well, the top portion forms a lid to the bottom portion, the top portion is pivotably coupled to the bottom portion and is movable between a first closed position and a second open position, the bottom portion and the top portion each comprise a plurality of openings, wherein the plurality of tissue cassettes include pre-assigned identifying indicia, wherein the pre-assigned identifying indicia comprise human readable characters indicating the body sites from where the prostate biopsy tissue samples are to be collected, wherein a plurality of human readable characters uniquely describing the different prostate gland locations to be sampled are pre-assigned and marked on each of the plurality of tissue cassettes of the tissue kit prior to use of the tissue kit, wherein each tissue cassette corresponds to a unique body site such that when prostate gland tissue samples are collected by the physician the source of a tissue sample placed directly into each of the plurality of tissue cassettes of the tissue kit corresponds to the pre-assigned identifying indicia indicating the unique body site marked on each of the plurality of tissue cassettes; and at least one vessel containing a fixative, the at least one vessel comprises a first vessel having a size and configuration sufficient to hold at least half of the plurality of tissue cassettes of the tissue kit after the tissue samples have been placed directly into the plurality of tissue cassettes, wherein the amount of fixative within the first vessel is less than 280 ml but is sufficient to preserve the tissue samples retained within the at least half of the plurality of tissue cassettes when the tissue cassettes are positioned within the first vessel prior to histological processing.

20. The tissue kit of claim 19, wherein the identifying indicia comprise a bar code.

21. The tissue kit of claim 19, wherein at least a portion of the identifying indicia is associated with a patient.

22. The tissue kit of claim 19, wherein at least a portion of the identifying indicia is associated with a pathology accession number.

23. The tissue kit of claim 19, wherein a first cassette comprises a first color and a second cassette comprises a second color, the second color being different from the first color.

24. The tissue kit of claim 19, wherein the at least one vessel further comprises a second vessel having a size and configuration sufficient to hold multiple tissue cassettes of the tissue kit after the tissue samples have been placed directly into the plurality of tissue cassettes, wherein an amount of fixative within the second vessel is less than 280 ml but is sufficient to preserve the tissue samples retained within the multiple tissue cassettes when the tissue cassettes are positioned within the second vessel prior to histological processing.

25. A tissue kit for taking one or more tissue samples for a biopsy, a resection, an excision and/or an autopsy analysis of a prostate, comprising:

a plurality of tissue cassettes configured to receive tissue samples from a patient, the plurality of tissue cassettes are adapted to retain the tissue samples during transport and during histological processing of the tissue samples, wherein each of the plurality of tissue cassettes has a bottom portion and a top portion, the bottom portion defines at least one tissue receiving well, the top portion forms a lid to the bottom portion, wherein the plurality of tissue cassettes include pre-assigned identifying indicia, wherein at least a portion of the pre-assigned identifying indicia comprises human readable characters indicating the body sites from where the tissue samples are to be collected, wherein a plurality of human readable characters uniquely describing the different locations to be sampled are pre-assigned and marked on each of the plurality of tissue cassettes of the tissue kit prior to use of the tissue kit, wherein each tissue cassette corresponds to a particular body site location such that when tissue samples are collected by the physician the source of a tissue sample placed into each of the plurality of tissue cassettes of the tissue kit corresponds to the pre-assigned identifying indicia indicating the particular body site marked on each of the plurality of tissue cassettes; and at least one vessel containing a fixative, the at least one vessel comprises a first vessel having a size and configuration sufficient to hold multiple tissue cassettes of the tissue kit after the tissue samples have been placed into the plurality of tissue cassettes, wherein the amount of fixative within the first vessel is sufficient to preserve the tissue samples retained within the multiple tissue cassettes when the multiple tissue cassettes are positioned within the first vessel.

26. The tissue kit of claim 25, wherein the identifying indicia comprise a bar code.

27. The tissue kit of claim 25, wherein the identifying indicia comprise a radio frequency device.

28. The tissue kit of claim 25, wherein the identifying indicia comprise a magnetic strip.

29. The tissue kit of claim 25, wherein a first cassette comprises a first color and a second cassette comprises a second color, the second color being different from the first color.

30. The tissue kit of claim 25, wherein the at least one vessel further comprises a second vessel having a size and configuration sufficient to hold multiple tissue cassettes of the tissue kit after the tissue samples have been placed directly into the plurality of tissue cassettes, wherein an amount of fixative within the second vessel is sufficient to preserve the tissue samples retained within the multiple tissue cassettes when the multiple tissue cassettes are positioned within the second vessel prior to histological processing.

31. A tissue kit for taking one or more tissue samples for a prostate biopsy analysis, comprising:
   a plurality of tissue cassettes, each of the plurality of tissue cassettes has a bottom portion and a top portion, the bottom portion defines at least one tissue receiving well, the top portion forms a lid to the bottom portion, wherein the plurality of tissue cassettes include pre-assigned identifying indicia, wherein the pre-assigned identifying indicia is associated with the tissue kit prior to use of the tissue kit, and wherein the pre-assigned identifying indicia comprise information about one or more of a specific individual, a specific tissue sample, a specific organ, a specific area of an organ, a specific pathology analysis method, a specific physician, or a specific pathology laboratory accession number, wherein at least a portion of the pre-assigned identifying indicia comprises human readable characters indicating the body sites from where the tissue samples are to be collected, wherein each tissue cassette corresponds to a single body site location, wherein a plurality of human readable characters uniquely describing the different locations to be sampled are pre-assigned and marked on each of the plurality of tissue cassettes of the tissue kit prior to use of the tissue kit, such that when tissue samples are collected by the physician the source of a tissue sample placed directly into each of the plurality of tissue cassettes of the tissue kit corresponds to the pre-assigned identifying indicia indicating the body site marked on each of the plurality of tissue cassettes; and
   a plurality of vessels containing a fixative, the plurality of vessels comprising at least a first vessel and a second vessel, each of the first and second vessel having a size and configuration sufficient to hold multiple tissue cassettes of the tissue kit after the tissue samples have been placed directly into the plurality of tissue cassettes, wherein the amount of fixative within each of the first and second vessels is sufficient to preserve the tissue samples retained within the multiple tissue cassettes when the multiple tissue cassettes are positioned respectively within the first vessel and within the second vessel.

32. The tissue kit of claim 31, wherein at least a portion of the pre-assigned identifying indicia is machine readable.

33. The tissue kit of claim 31, further comprising instructions for collecting tissue samples using the tissue kit.

34. The tissue kit of claim 31, wherein one or more tissue cassettes comprise a plurality of wells.

35. The tissue kit of claim 31, further comprising a needle.

36. The tissue kit of claim 31, wherein the plurality of tissue cassettes comprises from 2 to 14 cassettes.

37. A method of making a tissue kit for use in biopsy tissue collection, comprising:
   a) providing a plurality of tissue cassettes;
   b) associating pre-assigned identifying indicia with the plurality of tissue cassettes; and
   c) assembling the plurality of tissue cassettes into the tissue kit; and
   d) providing a plurality of vessels containing fixative and assembling the plurality of vessels into the tissue kit;
   wherein the pre-assigned identifying indicia comprise information about one or more of a specific individual, a specific tissue sample, a specific organ, a specific area of an organ, a specific pathology analysis method, a specific physician, or a specific pathology laboratory accession number, wherein at least a portion of the pre-assigned identifying indicia comprises human readable characters indicating the body sites from where the tissue samples are to be collected, wherein each tissue cassette corresponds to a single body site location, wherein a plurality of human readable characters uniquely describing the different locations to be sampled are pre-assigned and marked on each of the plurality of tissue cassettes of the tissue kit prior to use of the tissue kit, such that when tissue samples are collected by the physician the source of a tissue sample placed directly into each of the plurality of tissue cassettes of the tissue kit corresponds to the pre-assigned identifying indicia indicating the body site marked on each of the plurality of tissue cassettes; and wherein the plurality of vessels comprises at least a first vessel and a second vessel, each of the first and second vessel having a size and configuration sufficient to hold multiple tissue cassettes of the tissue kit.

38. The method of claim 37, wherein the identifying indicia comprise a linear bar code.

39. The method of claim 37, wherein the identifying indicia comprise a multi-dimensional bar code.

40. The method of claim 37, wherein a first cassette comprises a first color and a second cassette comprises a second color, the second color being different from the first color.

41. The method of claim 37, wherein the plurality of tissue cassettes comprises from 2 to 14 cassettes.

42. The method of claim 37, wherein the plurality of tissue cassettes comprises from 6 to 20 cassettes.

* * * * *